US011725038B2

(12) United States Patent
Cascio et al.

(10) Patent No.: US 11,725,038 B2
(45) Date of Patent: *Aug. 15, 2023

(54) TARGETED DELIVERY OF GLYCINE RECEPTORS TO EXCITABLE CELLS

(71) Applicant: University of Pittsburgh—of the Commonwealth System of Higher Education, Pittsburgh, PA (US)

(72) Inventors: Michael Cascio, Pittsburgh, PA (US); Joseph C. Glorioso, III, Blawnox, PA (US); James R. Goss, Bethel Park, PA (US); David Krisky, Sewickley, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 527 days.

This patent is subject to a terminal disclaimer.

(21) Appl. No.: 16/882,147

(22) Filed: May 22, 2020

(65) Prior Publication Data
US 2021/0040172 A1 Feb. 11, 2021

Related U.S. Application Data

(60) Continuation of application No. 14/584,895, filed on Dec. 29, 2014, now Pat. No. 10,696,727, which is a division of application No. 13/043,195, filed on Mar. 8, 2011, now Pat. No. 8,957,036, which is a division of application No. 12/152,310, filed on May 14, 2008, now abandoned.

(60) Provisional application No. 60/917,752, filed on May 14, 2007.

(51) Int. Cl.
C07K 14/705 (2006.01)
C12N 15/86 (2006.01)
A61K 48/00 (2006.01)
A01K 67/027 (2006.01)
C12N 7/00 (2006.01)
A61K 38/00 (2006.01)

(52) U.S. Cl.
CPC ........ C07K 14/705 (2013.01); A01K 67/0278 (2013.01); A61K 48/005 (2013.01); C12N 7/00 (2013.01); C12N 15/86 (2013.01); A01K 2217/20 (2013.01); A01K 2217/206 (2013.01); A01K 2227/105 (2013.01); A01K 2267/0356 (2013.01); A01K 2267/0393 (2013.01); A61K 38/00 (2013.01); C12N 2710/16643 (2013.01); C12N 2800/30 (2013.01)

(58) Field of Classification Search
CPC ..... A61K 48/00; A61K 48/005; C07K 14/705
USPC ...................................... 514/44 R
See application file for complete search history.

(56) References Cited

U.S. PATENT DOCUMENTS

| | | | |
|---|---|---|---|
| 5,658,724 | A | 8/1997 | DeLuca |
| 5,804,413 | A | 9/1998 | DeLuca |
| 5,837,532 | A | 11/1998 | Preston et al. |
| 5,849,571 | A | 12/1998 | Glorioso et al. |
| 5,849,572 | A | 12/1998 | Glorioso et al. |
| 5,879,934 | A | 3/1999 | DeLuca |
| 5,998,174 | A | 12/1999 | Glorioso et al. |
| 6,261,552 | B1 | 7/2001 | DeLuca |
| 7,056,737 | B2 | 6/2006 | Feder et al. |
| 7,078,029 | B2 | 7/2006 | DeLuca |
| 2003/0083289 | A1 | 5/2003 | Boursnell et al. |
| 2004/0092498 | A1 | 5/2004 | Blakemore et al. |
| 2005/0209317 | A1 | 9/2005 | Apkarian |
| 2007/0092510 | A1 | 4/2007 | DeKonnick et al. |

FOREIGN PATENT DOCUMENTS

| | | |
|---|---|---|
| WO | WO 91/02788 A1 | 3/1991 |
| WO | WO 96/04394 A1 | 2/1996 |
| WO | WO 98/15637 A1 | 4/1998 |
| WO | WO 99/06583 A1 | 2/1999 |
| WO | WO 00/75292 A1 | 12/2000 |
| WO | WO 02/097092 A1 | 12/2002 |

OTHER PUBLICATIONS

Amaya (The Journal of Neuroscience, 2006, 26:12852-12860.*
Betz et al., Journal of Neurochemistry, 97: 1600-1610 (2006).
Bradley et al., Nature, 309: 255-256 (May 17, 1984).
Braz et al., "Therapeutic Efficacy in Experimental Polyarthritis of Viral-Driven Enkephalin Overproduction in Sensory Neurons," The Journal of Neuroscience, 21(20): 7881-7888 (Oct. 15, 2001).
Cascio et al., The Journal of Biological Chemistry, 268(29): 22135-22142 (Oct. 15, 1993).
Cascio, The Journal of Biological Chemistry, 279(19): 19383-19386 (May 7, 2004).
Cascio et al., "Targeted Delivery of Glycine Receptors to Peripheral Neurons as Treatment for Pain," Biophysical Journal, 96(3) Supplement 1: 487a (2009).
Chaplan et al., Journal of Neuroscience Methods, 53(1): 55-63 (Jul. 1994).
Chaplan et al., The Journal of Pharmacology and Experimental Therapeutics, 269(3): 1117-1123 (1994).

(Continued)

Primary Examiner — Valarie E Bertoglio
(74) Attorney, Agent, or Firm — Leydig, Voit & Mayer, Ltd.

(57) ABSTRACT

The invention provides a method of modulating electrophysiological activity of an excitable cell. The method involves causing exogenous expression of a glycine receptor (GlyR) protein in an excitable cell of a subject. Thereafter, the excitable cell is exposed to an allosteric modulator of the GlyR protein. Modulation of the exogenous GlyR protein (an ion channel) in response to the allosteric modulator modulates the electrophysiological activity of the excitable cell. The method can be used to control pain in a subject. The invention further provides a replication-defective HSV vector comprising an expression cassette encoding a GlyR protein, stocks and pharmaceutical compositions containing such vectors, and a transgenic animal.

13 Claims, 4 Drawing Sheets

(56) References Cited

OTHER PUBLICATIONS

Cheng et al., "Homology Modeling and Molecular Dynamics Simulations of the α1 Glycine Receptor Reveals Different States of the Channel," *Proteins*, 68: 581-593 (2007).
Cheng et al., "Molecular dynamics simulations of ethanol binding to the transmembrane domain of the glycine receptor: Implications for the channel potentiation mechanism," *Proteins*, 71: 972-981 (2008).
Coull et al., *Nature*, 438: 1017-1021 (Dec. 15, 2005).
De Koninck, *Current Opinion in Pharmacology*, 7: 93-99 (2007).
Deleuze et al., *Neuroscience*, 133: 175-183 (2005).
Dubin et al., Nociceptors: the sensors of the pain pathway, J Clin Invest., 120 (11) 3760-72 (2010).
Dubuisson et al., *Pain*, 4(2): 161-174 (1977).
Enna et al., *Advances in Pharmacology*, 54: 1-27 (2006).
Evans et al., *Nature*, 292: 154-156 (Jul. 9, 1981).
Fink et al., "Engineering herpes simplex virus vectors for gene transfer to neurons," *Nature Medicine*, 3(3): 357-359 (Mar. 1997).
Glorioso et al., "Use of HSV vectors to modify the nervous system," *Current Opinion in Drug Discovery & Development*, 5(2): 289-295 (2002).
Goss et al., *Gene Therapy*, 8: 551-556 (2001).
Goss et al., *Annals of Neurology*, 52(5): 662-665 (Nov. 2002).
Goss et al., "HSV Delivery of a Ligand-regulated Endogenous Ion Channel Gene to Sensory Neurons Results in Pain Control Following Channel Activation," *Molecular Therapy*, 19(3): 500-506 (Mar. 2011).
Gossler et al., *Proc. Natl. Acad. Sci. USA*, 83: 9065-9069 (Dec. 1986).
Grudzinska et al., *Neuron*, 45: 727-739 (Mar. 3, 2005).
Hao et al., "Gene Transfer of Glutamic Acid Decarboxylase Reduces Neuropathic Pain," *Annals of Neurology*, 57(6): 914-918 (Jun. 2005).
Harvey et al., *Science*, 304: 884-887 (May 7, 2004).
Hemmings et al., *Trends in Pharmacological Sciences*, 26(10): 503-510 (Oct. 2005).
Hirzel et al., *Neuron*, 52: 679-690 (Nov. 22, 2006).
Iadarola et al., *Brain*, 121(Pt.5): 931-947 (May 1998).
Ishikawa et al., *Neuroscience*, 95(3): 781-786 (2000).
Jaenisch, *Science*, 240(4858): 1468-1474 (Jun. 10, 1988).
Keramidas et al., *J. Gen. Physiol.*, 119: 393-410 (May 2002).
Kirsch, *Cell Tissue Res.* 326: 535-540 (2006).
Lerchner et al., "Reversible Silencing of Neuronal Excitability in Behaving Mice by a Genetically Targeted, Ivermectin-Gated $Cl^{31}$ Channel," *Neuron*, 54: 35-49 (Apr. 5, 2007).
Lynagh et al., "An Improved Ivermectin-activated Chloride Channel Receptor for Inhibiting Electrical Activity in Defined Neuronal Populations," *Journal of Biological Chemistry*, 285(20): 14890-14897 (May 14, 2010).
Lynch et al., *Current Opinion in Investigational Drugs*, 7(1): 48-53 (Jan. 2006).
McGeoch et al., *J. Gen. Virol.*, 69(Pt.7): 1531-1574 (1988).
Meier et al., *Nature Neuroscience*, 8(6): 736-744 (Jun. 2005).
Mohammadi et al., *Eur. Biophys. J.*, 32: 529-536 (2003).
NCBI "Mus Musculus Glycine Receptor Alpha 3 Subunit (Glra3) mRNA, Complete cds." Database Entrez-Nucleotide, Accession No. AF362764 (Aug. 9, 2001). Retrieved on Jul. 29, 2008.
NCBI "Mus Musculus Glycine Receptor Alpha 3 Subunit (Glra3) mRNA, Complete cds." Database Entrez Nucleotide, Accession No. AY230204 (Jun. 1, 2003). Retrieved on Jul. 29, 2008.
NCBI "Homo Sapiens Glycine Receptor, Alpha 3, mRNA (cDNA clone MGC: 33772 IMAGE:5286731), Complete cds." Database Entrez Nucleotide, Accession No. BC036086 (Jul. 21, 2006). Retrieved on Jul. 29, 2008.
NCBI "Mus Musculus Glycine Receptor, Alpha 4 Subunit, mRNA (cDNA clone MGC:130223 IMAGE:40052661), Complete cds." Database Entrez Nucleotide, Accession No. BC110630 (Oct. 4, 2006). Retrieved on Jul. 29, 2008.
NCBI "Homo Sapiens Full Open Reading Frame cDNA Clone RZPDo834E082D For Gene GLRA2, Glycine Receptor, Alpha 2; Complete cds; Without stopcodon," Database Entrez Nucleotide, Accession No. CR450343 (May 18, 2004). Retrieved on Jul. 29, 2008.
NCBI "Human Herpesvirus 1, Complete Genome," Database Entrez Nucleotide, Accession No. NC_001806 (Aug. 13, 2007). Retrieved on Jul. 29, 2008.
NCBI "Homo Sapiens Glycine Receptor, Alpha 1 (GLRA1), mRNA," Database Entrez Nucleotide, Accession No. NM_000171 (Jun. 29, 2008). Retrieved on Jul. 29, 2008.
NCBI "Homo Sapiens Glycine Receptor, Beta (GLRB), mRNA," Database Entrez Nucleotide, Accession No. NM 000824 (Mar. 16, 2008). Retrieved on Jul. 29, 2008.
NCBI "Homo Sapiens Glycine Receptor, Alph 2 (GLRA2), Transcript Variant 1, mRNA," Database Entrez Nucleotide, Accession No. NM_002063 (Mar. 7, 2008) Retrieved on Jul. 29, 2008.
NCBI "HomoSapiens Glycine Receptor, Alpha 3 (GLRA3), Transcript Variant 1, mRNA," Database Entrez Nucleotide, Accession No. NM_006529 (Mar. 16, 2008) Retrieved on Jul. 29, 2008.
NCBI "Mus Musculus Glycine Receptor, Alpha 4 Subunit (Glra4), mRNA," Database Entrez Nucleotide, Accession No. NM_010297 (Jul. 19, 2008) Retrieved on Jul. 29, 2008.
NCBI "Mus Musculus Glycine Receptor, Beta Subunit (Glrb), mRNA," Database Entrez Nucleotide, Accession No. NM_010298 (Jul. 20, 2008). Retrieved on Jul. 29, 2008.
NCBI "Rattus Norvegicus Glycine Receptor, Alpha 2 Subunit (Glra2), mRNA," Database Entrez Nucleotide, Accession No. NM_012568 (Jul. 13, 2008) Retrieved on Jul. 29, 2008.
NCBI "Rattus Norvegicus Glycine Receptor, Alpha 1 Subunit (Gira1), mRNA," Database Entrez Nucleotide, Accession No. NM_013133 (Feb. 10, 1008). Retrieved on Jul. 29, 2008.
NCBI "Rattus Norvegicus Glycine Receptor, Beta Subunit (Glrb), mRNA," Database Entrez Nucleotide, Accession No. NM_053296 (Apr. 29, 2008). Retrieved on Jul. 29, 2008.
NCBI "Mus Musculus Glycine Receptor, Alpha 2 Subunit (Glra2), mRNA," Database Entrez Nucleotide, Accession No. NM_183427 (Apr. 6, 2008). Retrieved on Jul. 29, 2008.
NCBI "Mus Musculus Glycine Receptor, Alpha 1 Subunit (Gira1), mRNA," Database Entrez Nucleotide, Accession No. NM_020492 (Apr. 13, 2008). Retrieved on Jul. 29, 2008.
NCBI "Rattus Norvegicus Glycine Receptor, Alpha 3 Subunit (Glra3), mRNA," Database Entrez Nucleotide, Accession No. NM_053724 (Feb. 10, 2008). Retrieved on Jul. 29, 2008.
NCBI "Mus Musculus Glycine Receptor, Alpha 3 Subunit (Glra3), mRNA," Database Entrez Nucleotide, Accession No. NM_080438 (Apr. 6, 2008). Retrieved on Jul. 29, 2008.
NCBI "Homo Sapiens Glycine Receptor, Alpha 3 (GLRA3), Transcript Variant 2, mRNA," Database Entrez Nucleotide, Accession No. NM_001042543 (May 1, 2008). Retrieved on Jul. 29, 2008.
Qian et al., *Journal of Physiology*, 538(1): 65-77 (2002).
Qian et al., *Journal of Physiology*, 562(2): 319-331 (2005).
Rajendra et al., *Neuron*, 14: 169-175 (Jan. 1995).
Rajendra et al., *Pharmacol. Ther.*, 73(2): 121-146 (1997).
Robertson et al., *Nature*, 323:445-448 (Oct. 2, 1986).
Schmieden et al., *Science*, 262(5131): 256-258 (Oct. 8, 1993).
Shan et al., "Ivermectin, an unconventional agonist of the glycine receptor chloride channel", J Biol Chem, 276(16): 12556-64 (2001).
Sivilotti et al., *Journal of Neurophysiology*, 72(1): 169-179 (Jul. 1994).
Slimko et al., *The Journal of Neuroscience*, 22(17): 7373-7379 (Sep. 1, 2002).
Sontheimer et al., *Neuron*, 2: 1491-1497 (May 1989).
Speranskiy et al., "Homology Modeling and Molecular Dynamics Simulations of the Glycine Receptor Ligand Binding Domain," *Proteins*, 67: 950-960 (2007).
Stirling et al., *Pain*, 113(1-2): 27-36 (2007).
Thio et al., *Neuroscience*, 739: 1315-1327 (2006).
Willis, *Progress in Neurobiology*, 78: 189-214 (2006).
Zinyk et al., *Current Biology*, 8(11): 665-668, S1-S4 (1998).

(56) References Cited

OTHER PUBLICATIONS

International Search Report dated Aug. 8, 2008, in PCT/US2008/006152.
Written Opinion dated Aug. 8, 2008, in PCT/US2008/006152.

* cited by examiner

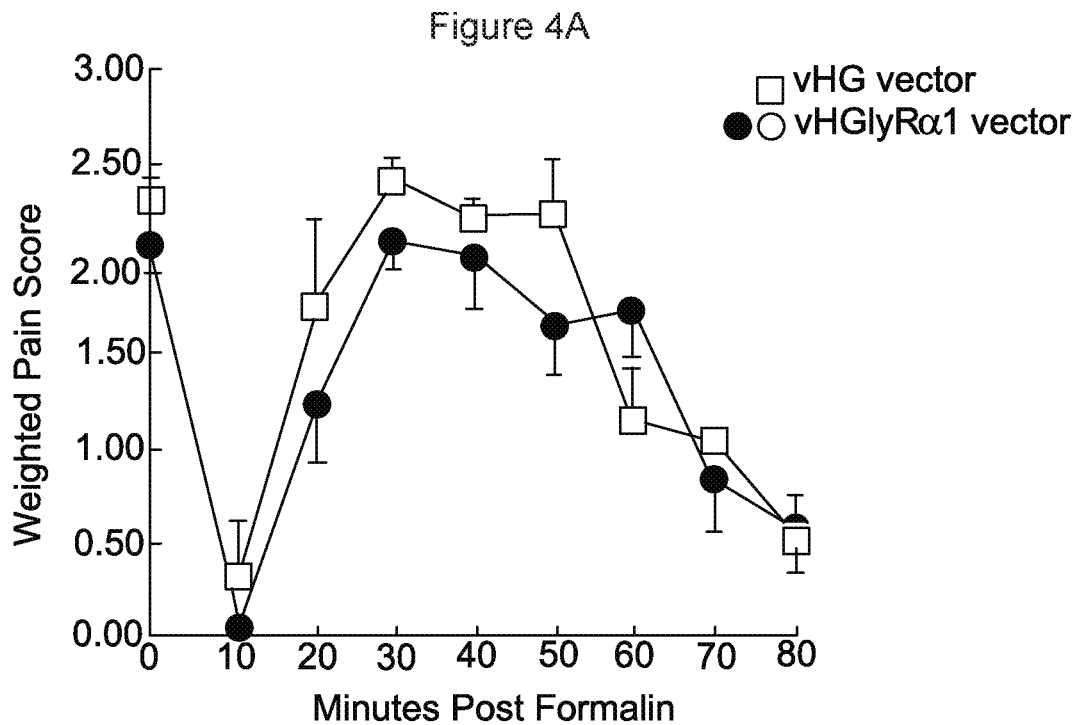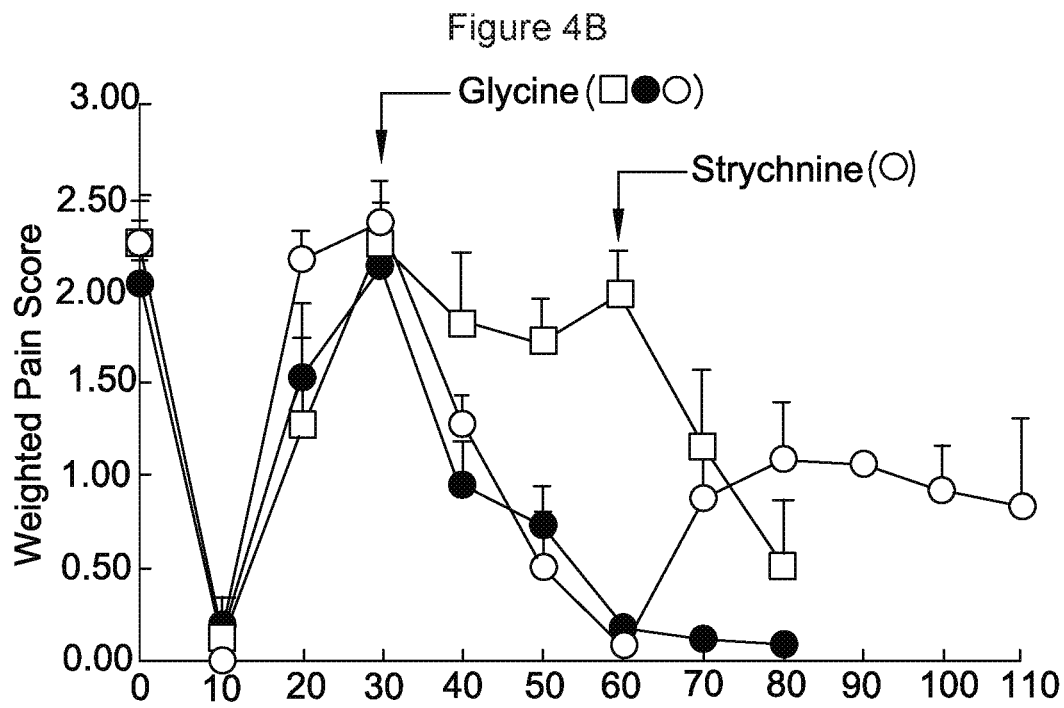

TARGETED DELIVERY OF GLYCINE RECEPTORS TO EXCITABLE CELLS

CROSS-REFERENCE TO RELATED APPLICATIONS

This patent application is a continuation of copending U.S. patent application Ser. No. 14/584,895, filed Dec. 29, 2014, now U.S. Pat. No. 10,696,727, which is a divisional of U.S. patent application Ser. No. 13/043,195, filed Mar. 8, 2011, now U.S. Pat. No. 8,957,036, which is a divisional of U.S. patent application Ser. No. 12/152,310, filed May 14, 2008, now abandoned, which claims the benefit of U.S. Provisional Patent Application No. 60/917,752, filed May 14, 2007, each of which is incorporated by reference herein in its entirety.

STATEMENT REGARDING FEDERALLY SPONSORED RESEARCH AND DEVELOPMENT

This invention was made with Government support under Grant Number DK044935 awarded by the National Institutes of Health. The Government has certain rights in this invention.

BACKGROUND OF THE INVENTION

The potential to modulate the electrophysiological response of excitable cells (such as neurons and muscle cells) could potentially lead to treatment of neuromuscular conditions, pain, and other disorders associated with the activity of such cells. However, the administration of ligands that act on endogenous ion channels poses significant hurdles because of the potential for widespread side effects due to systemic delivery. Moreover, agents that act locally (such as silver or capsaicin) have unwanted side effects and can potentially cause permanent damage.

Modulation of neuronal activity by expression of a ligand-gated anionic channel has been shown previously wherein expression of a glutamate-gated chloride channel (GluCl), a nicotinicoid family receptor found in invertebrates, was used to silence neurons (Slimko et al., *J. Neurosci.*, 22, 7373-9 (2002)). GluCl could be selectively activated by the addition of ivermectin, a high-potency ligand that has little or no effects on endogenous mammalian ion channels at low concentrations. For use in vertebrates, and particularly in human patients, however, this approach poses a risk of generating an immune response against such a foreign protein, leading to potential autoimmune disorders. Accordingly, additional methods and reagents for modulating the electrophysiological activity of excitable cells are desired.

BRIEF SUMMARY OF THE INVENTION

The invention provides a method and reagents for modulating the electrophysiological activity of an excitable cell. The method involves causing exogenous expression of a glycine receptor (GlyR) protein in an excitable cell of a subject. Thereafter, the excitable cell is exposed to an allosteric modulator of the GlyR protein. Modulation of the exogenous GlyR protein (an ion channel) in response to the allosteric modulator modulates the electrophysiological activity of the excitable cell. The method can be used to control pain in a subject. The invention further provides a replication-defective HSV vector comprising an expression cassette encoding a GlyR protein and stocks and pharmaceutical compositions containing such vectors. The invention further provides a transgenic animal comprising an exogenously expressed GlyR protein. These aspects and other inventive features are further addressed in the accompanying drawings and the following detailed description.

BRIEF DESCRIPTION OF THE SEVERAL VIEWS OF THE DRAWING(S)

Figure 3:
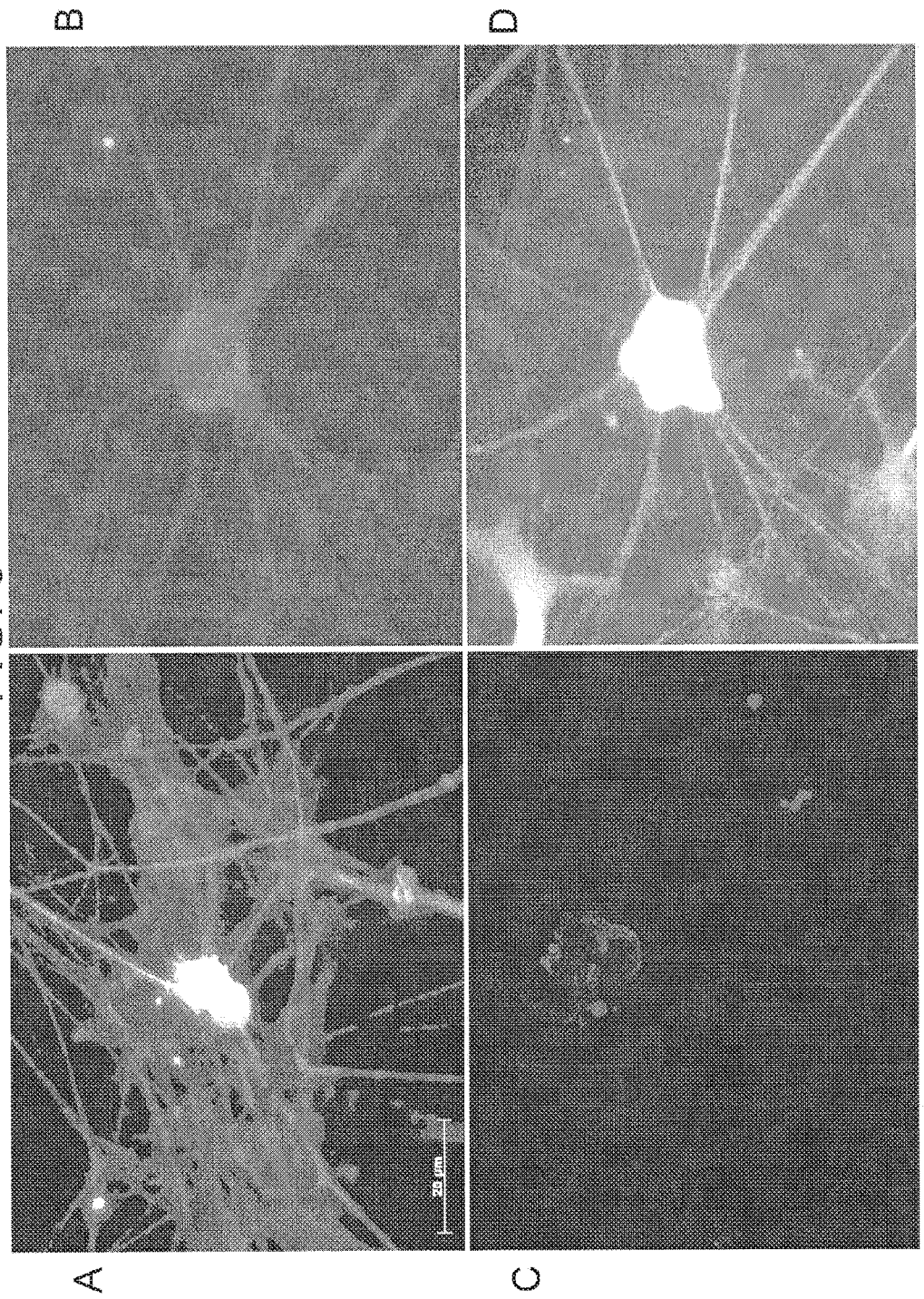

FIG. 3 is an image depicting exogenous expression of α1 subunit of GlyR in primary dorsal root ganglion (DRG) neurons. Neurons were infected with vHGlyRα1 (panel A), vHG (panel B), or a vector encoding green fluorescent protein (GFP) (panel D). Neurons incubated without the primary antibody are shown in panel C.

FIG. 4A is a graph demonstrating that exogenously applied glycine reduces formalin-induced nociceptive behavior in rats following injection of a GlyR-expressing HSV vector.

FIG. 4B is a graph demonstrating that exogenously applied glycine reduces formalin-induced nociceptive behavior in rats following injection of a GlyR-expressing HSV vector, and that alleviation of observed pain was reversed by strychnine injection.

DETAILED DESCRIPTION OF THE INVENTION

In one embodiment, the invention provides a method of modulating the electrophysiological activity of an excitable cell. The method involves causing exogenous expression of a glycine receptor (GlyR) protein in an excitable cell of a subject. Thereafter, the excitable cell is exposed to an allosteric modulator of the GlyR protein. Modulation of the exogenous GlyR protein (an ion channel) in response to the allosteric modulator modulates the electrophysiological activity of the excitable cell.

The excitable cell can be any cell that experiences fluctuations in its membrane potential as a result of gated ion channels. Such cells can include myocytes, neurons, and the like. However, the inventive method is particularly well suited for application to peripheral neurons.

The method typically is applied to excitable cells of mammalian subjects, but can be applied to subjects of other chordate phyla (e.g., avians, reptiles, amphibians, bony and cartilaginous fish, etc.). Indeed, employment of the method in such creatures as well as common laboratory mammals (e.g., mice, rats, guinea pigs, dogs, monkeys, apes, etc.) can be useful in biomedical research. Typically, however the method is employed in connection with excitable cells of mammals, and can be used medically in human patients (subjects) (e.g., to treat pain). The method also can be practiced on veterinary patients (subjects) such as cats, dogs, pigs, horses, cattle, sheep, and the like.

The inventive method desirably is used to attenuate the sensation of pain in a subject (preferably a human subject). The pain can be isolated pain, or the pain can be associated with a particular disease. The pain can be associated with any known human disease, including but not limited to, diabetes, arthritis, cardiovascular disease, autoimmune disease, respiratory disease (e.g., emphysema), infectious disease (e.g., viral or bacterial infections), neurological disease (e.g., Alzheimer's disease), gastrointestinal disease, liver disease, blood disorders, allergies, endocrine disease, and cancer. The pain can be associated with cancer of the oral cavity (e.g., tongue cancer and mouth cancer), the pharynx, the digestive system (e.g., the esophagus, stomach, small intestine, colon, rectum, anus, liver, gall bladder, and pancreas), the respiratory system (e.g., lung cancer), bones and joints (e.g., bony metastases, osteosarcoma), soft tissue, the skin (e.g., melanoma), breast, the genital system (e.g., ovarian cancer), the urinary system (e.g., bladder cancer, renal cancer), the eye and orbit, the brain and nervous system (e.g., glioma), or the endocrine system (e.g., thyroid). The cancer also can be a lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like).

The GlyR protein is exogenous in the sense that it is not natively expressed in the excitable cell to be treated in accordance with the inventive method. Generally, GlyRs are expressed primarily in cells within the spinal cord and lower brain. Thus, where even a wild-type GlyR protein (i.e., other than a mutein) is expressed in, for example, peripheral neurons, its expression in such cells is exogenous. Also, exogenous expression can be expression of a GlyR protein at significantly higher levels than wild-type expression. Thus, inducement of expression of a GlyR protein in a cell expressing the GlyR protein at a low level is regarded as "exogenous" if the excitable cell is induced to produce measurably more GlyR protein as a result of the induction.

Any suitable method can be employed to cause or induce exogenous expression of the GlyR protein in the excitable cell. For example, an agent can be applied to the excitable cell that activates transcription of the gene encoding the GlyR protein from the genome of the excitable cell. However, preferably, exogenous expression of the GlyR protein is caused or induced by gene transfer technology. In this respect, the method can involve introducing a genetic vector into the excitable cell, which vector comprises an expression cassette including a nucleic acid encoding the GlyR protein.

The GlyR is a member of the nicotinicoid superfamily of ligand-gated ionotropic receptors that mediate fast neurotransmission in the central nervous system (CNS). In the case of the GlyR, binding of glycine ($EC_{50}$ of 20 μM-100 μM) or other agonists leads to transient gating of this anion-selective channel. In adults, the GlyR is believed to typically have a stoichiometry of 2 α subunits and 3 β subunits. Heterologous expression of just the human α1 subunit, however, is sufficient to reconstitute an active glycine-gated channel with pharmacological properties essentially identical to those of native channels. Accordingly, for use in the inventive method, the GlyR protein can be a wild-type subunit of GlyR (e.g., alpha1, alpha2, alpha3, alpha4, or beta), and is preferably a subunit of mammalian origin or a mutein of such subunit. The GlyR proteins are well characterized (Rajendra et al., *Pharmacol. Ther.,* 73(2): 121-46 (1997)) and the sequences encoding many subunits from mammalian species are indexed in genetic databases or are otherwise available. For example, sequences relating to the alpha1 subunit of GlyR can be found at NCBI Accession Nos. NM_000171 (human), NM_020492 (mouse) and NM_013133 (rat). Sequences relating to the alpha2 subunit of GlyR can be found at NCBI Accession Nos. NM_002063 (human), CR450343 (cDNA) (human)), NM_183427 (mouse), and NM_012568 (rat). Sequences relating to the alpha3 subunit of GlyR can be found at NCBI Accession Nos. NM_006529 (human), NM_001042543 (human), BC036086 (human), NM_080438 (mouse), AY230204 (mouse), AF362764 (mouse), and NM_053724 (rat). Sequences relating to the alpha4 subunit of GlyR can be found at NCBI Accession Nos. NM_010297 (mouse), and BC110630 (mouse). Sequences relating to the beta subunit of GlyR can be found at NCBI Accession Nos. NM_000824 (human), NM_010298 (mouse), and NM_053296 (rat).

In addition to wild-type GlyR subunits, mutant forms of GlyR subunit with altered activity (muteins) also are known, and can be used in the context of the present invention. In this regard, the GlyR protein can comprise a mutein of any of the GlyR subunits. For example, certain muteins of GlyR proteins result in altered ion-channel properties, such as resulting in a cationic ion channel (e.g., Δ250 A251E Keramidas et al., *J. Gen. Physiol.,* 119, 393 (2002)). Other muteins are known that lack sites for zinc potentiation or zinc inhibition (Hirzel et al., *Neuron,* 52, 679-90 (2006)), affinity for allosteric modulators (e.g., anesthetic potentiation (Hemmings et al., *Trends Pharmacol. Sci.,* 26, 503-10 (2005)), or affinity for ligands (Rajendra et al., *Neuron,* 14, 169-175 (1995); Schrnieden et al., *Science,* 262, 256-258 (1993)). Mutation of GlyR subunits also can selectively alter ion permeation (e.g., anionic- or cationic-selective channels), and redesign a receptor subunit's ligand binding pockets to recognize unique pharmacologic agents. For example, to alter the sensitivity and selectivity of a GlyR protein for a particular ligand, point mutations can be made in the GlyRα1 subunit that are expected to shift the dose response curve to the left or right (i.e., less or more specific to glycine). Other mutations can alter the sensitivity of a GlyR protein to certain anesthetics (e.g., ethanol). For example, a mutation in the mouse glycine α1 receptor subunit in which a methionine (M) at position 287 is changed to leucine (L) (M297L) results in greatly enhanced sensitivity to the volatile anesthetic enflurane. Such GlyR muteins can be employed as the GlyR protein in the context of the present invention.

Mutant forms of GlyR subunits can be generated using any suitable method known in the art. Such methods include, for example, site-directed mutagenesis, random mutagenesis by PCR, linker-scanning mutagenesis of DNA, and chemical mutagenesis (see, e.g., Ausubel et al., eds., *Short Protocols in Molecular Biology,* 5$^{th}$ Ed., John Wiley & Sons, Inc. (2002)).

Any suitable vector for introducing the expression cassette encoding the GlyR protein into the excitable cell can be employed. Examples of suitable vectors include plasmids, liposomes, molecular conjugates (e.g., transferrin), and viruses. Preferably, the vector is a viral vector. Suitable viral vectors include, for example, retroviral vectors, herpes virus based vectors and parvovirus based vectors (e.g., adeno-associated virus (AAV) based vectors, AAV-adenoviral chimeric vectors, and adenovirus-based vectors). Most preferably, the vector is a replication-defective (also referred to as "replication-deficient") herpes simplex virus (HSV) vector.

A vector comprising an expression cassette including a nucleic acid encoding the GlyR protein can facilitate transfer of the GlyR expression cassette to the excitable cell by infecting (or transfecting, as appropriate) the excitable cell with the vector. Given their neurotropic properties, replication-deficient HSV-based vector systems can be used to deliver the GlyR expression cassette to the excitable cell by peripheral inoculation. Following inoculation of a site on the skin, mucus membrane, or other peripheral site, replication-deficient HSV vectors infect the excitable cell, which facilitates expression of the GlyR protein within the infected excitable cell. However, because such vectors are replication-defective, they do not replicate within the excitable cell to spread to other areas. In this sense, where replication-defective HSV vectors are employed to deliver the GlyR gene, a site of inoculation can be selected to target the treatment to a pre-selected area.

In further performance of the inventive method, an allosteric modulator or ligand of the GlyR protein is exposed to the excitable cell in which the exogenous GlyR protein is exogenously expressed. The allosteric modulator can, for example, agonize or antagonize (open or close) the GlyR channel, which in turn alters the electrophysiology of the excitable cell. A preferred agonist is glycine; however other suitable agonists of the GlyR protein (e.g., taurine and beta-alanine) can be employed. Also, a suitable antagonist is strychnine; however other antagonists can be employed. The allosteric modulator can be delivered systemically (e.g., parenterally). However, it is preferred for the allosteric modulator to be administered locally (regionally) to the area encompassing the excitable cell exogenously expressing the GlyR. Particularly where replication-defective HSV vectors are employed, the ability to target specific areas, coupled with the limited distribution of endogenous GlyRs, permits regional delivery of GlyR-specific allosteric modulators at concentrations sufficient to activate the receptor and should not lead to unwanted side effects.

The introduction of a ligand-gated ionotropic receptor (GlyR) that can be quickly and reversibly activated or inhibited via addition of exogenous ligands, thereby allowing the permeation of select ions, can manipulate the resting potential of excitable cells, and hence their function. The method can be used in many contexts. In one application, the inventive method can attenuate the sensation of pain in a patient. In this application, a vector containing an expression cassette encoding the GlyR protein (e.g., alpha1 subunit) is employed to cause exogenous expression of the GlyR protein within peripheral neurons, such as c-fibers, associated with the sensation of pain. Where a replication-defective HSV vector is employed, the vector can be injected into a portion of the subject's skin (e.g., a toe), mucus membrane, or other desired tissue to introduce the expression cassette encoding the GlyR protein into the peripheral neurons. Thereafter, glycine or another agonist of the GlyR protein can be injected into the area of the inoculation to reduce the sensation of pain associated with the peripheral neurons. The method can be used to reduce the local or regional sensation of pain in some subjects (patients) partially or completely.

In another embodiment, the inventive method can be used to generate a transgenic animal that exogenously expresses GlyR protein. The animal can be any animal that is amenable to modification and analysis via conventional transgenic technology, such as, for example, a zebrafish, mouse, rat, or pig. The transgenic animal can be generated using any suitable method known in the art. Typically and preferably, transgenic animals are generated using embryonic stem (ES) cell technology. ES cells are obtained by culturing preimplantation embryos in vitro under appropriate conditions (Evans et al., *Nature,* 292:154-156 (1981); Bradley et al., *Nature,* 309: 255-258 (1984); Gossler et al., *Proc. Acad. Sci.* (*USA*), 83: 9065-9069 (1986); and Robertson et al., *Nature,* 322: 445-448 (1986)). Transgenes can be efficiently introduced into the ES cells by DNA transfection by a variety of methods known to the art, including calcium phosphate co-precipitation, protoplast or spheroplast fusion, lipofectin and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (see, e.g., Jaenisch, *Science,* 240: 1468-1474 (1988)). Progeny animals carrying the transgene in their germline can be identified by Southern blot analysis, by polymerase chain reaction (PCR), and/or by Northern blot analysis. Transgenic animal technology is further described in, for example, Pinkett, *Transgenic Animal Technology: A Laboratory Handbook,* 2$^{nd}$ Ed., Academic Press (2002), and Hofker et al., eds., *Transgenic Mouse Methods and Protocols* (*Methods in Molecular Biology*), Human Press (2002)).

To facilitate the inventive method, the invention provides an HSV vector comprising an expression cassette encoding a GlyR protein. An HSV based viral vector is suitable for use as a vector to introduce a nucleic acid sequence into numerous cell types. The mature HSV virion consists of an enveloped icosahedral capsid with a viral genome consisting of a linear double-stranded DNA molecule that is 152 kb. In a preferred embodiment, the HSV based viral vector is deficient in at least one essential HSV gene. Of course, the vector can alternatively or in addition be deleted for non-essential genes. Preferably, the HSV based viral vector that is deficient in at least one essential HSV gene is replication-deficient. Most replication-deficient HSV vectors contain a deletion to remove one or more intermediate-early, early, or late HSV genes to prevent replication. For example, the HSV vector may be deficient in a gene selected from the group consisting of: ICP0, ICP4, ICP22, ICP27, ICP47, and a combination thereof. A preferred HSV vector is deficient for all immediate early genes except for ICP0. Advantages of the HSV vector are its ability to enter a latent stage that can result in long-term DNA expression and its large viral DNA genome that can accommodate exogenous DNA inserts of up to 25 kb.

HSV-based vectors and methods for their construction are described in, for example, U.S. Pat. Nos. 7,078,029, 6,261,552, 5,998,174, 5,879,934, 5,849,572, 5,849,571, 5,837,532, 5,804,413, and 5,658,724, and International Patent Applications WO 91/02788, WO 96/04394, WO 98/15637, and WO 99/06583, which are incorporated herein by reference. Preferably, the HSV vector is "multiply-deficient," meaning that the HSV vector is deficient in more than one gene function required for viral replication. The sequence of HSV is published (NCBI Accession No. NC_001806; see also McGoech et al., *J. Gen. Virol,* 69 (PT 7), 1531-1574 (1988)), which may facilitate the generation of desired mutations in designing HSV-based vectors.

The HSV vector can be deficient in replication-essential gene functions of only the early regions of the HSV genome, only the immediate-early regions of the HSV genome, only the late regions of the HSV genome, or both the early and late regions of the HSV genome. The HSV vector also can have essentially the entire HSV genome removed, in which case it is preferred that at least either the viral inverted terminal repeats (ITRs) and one or more promoters or the viral ITRs and a packaging signal are left intact (i.e., an HSV amplicon). The larger the region of the HSV genome that is removed, the larger the piece of exogenous nucleic acid sequence that can be inserted into the genome.

It should be appreciated that the deletion of different regions of the HSV vector can alter the immune response of the mammal. In particular, the deletion of different regions can reduce the inflammatory response generated by the HSV vector. Furthermore, the HSV vector's protein coat (i.e., one or more envelope proteins) can be modified so as to decrease the HSV vector's ability or inability to be recognized by a neutralizing antibody directed against the wild-type protein coat. In addition, one or more envelope proteins of the HSV vector can be modified so as to alter the binding specificity, attachment, and/or entry of the HSV vector to a particular cell. For HSV, such manipulations can include deletion of regions of any one of the ten glycoproteins (gB through gM) that make up the HSV envelope (e.g., glycoprotein C and/or glycoprotein D), or insertions of various native or non-native ligands into portions of an envelope glycoprotein. Manipulation of the envelope proteins can broaden the range of cells infected by the HSV vector or enable targeting of the HSV vector to a specific cell type.

The HSV vector, when multiply replication-deficient, can include a spacer element to provide viral growth in a complementing cell line similar to that achieved by singly replication-deficient HSV vectors. The spacer element can contain any nucleic acid sequence or sequences which are of the desired length. The spacer element sequence can be coding or non-coding and native or non-native with respect to the HSV genome, but does not restore the replication essential function(s) to the deficient region. In addition, the inclusion of a spacer element in any or all of the deficient HSV regions will decrease the capacity of the HSV vector for large inserts. The production of HSV vectors involves using standard molecular biological techniques well known in the art.

When the vector is a replication-deficient HSV, the nucleic acid sequence encoding the protein (e.g., GlyR protein) can be located in the locus of an essential HSV gene, such as either the ICP4 or the ICP27 gene locus of the HSV genome. The insertion of a nucleic acid sequence into the HSV genome (e.g., the ICP4 or the ICP27 gene locus of the HSV genome) can be facilitated by known methods, for example, by the introduction of a unique restriction site at a given position of the HSV genome.

Replication-deficient HSV vectors are typically produced in complementing cell lines that provide gene functions not present in the replication-deficient HSV vectors, but required for viral propagation, at appropriate levels in order to generate high titers of viral vector stock. A preferred cell line complements for at least one and preferably all replication-essential gene functions not present in a replication-deficient HSV vector. The cell line also can complement non-essential genes that, when missing, reduce growth or replication efficiency (e.g., UL55). The complementing cell line can complement for a deficiency in at least one replication-essential gene function encoded by the early regions, immediate-early regions, late regions, viral packaging regions, virus-associated regions, or combinations thereof, including all HSV functions (e.g., to enable propagation of HSV amplicons, which comprise minimal HSV sequences, such as only inverted terminal repeats and the packaging signal or only ITRs and an HSV promoter). The cell line preferably is further characterized in that it contains the complementing genes in a non-overlapping fashion with the HSV vector, which minimizes, and practically eliminates, the possibility of the HSV vector genome recombining with the cellular DNA. Accordingly, the presence of replication competent HSV is minimized, if not avoided in the vector stock, which, therefore, is suitable for certain therapeutic purposes, especially gene therapy purposes. The construction of complementing cell lines involves standard molecular biology and cell culture techniques well known in the art.

The expression of the nucleic acid sequence encoding the GlyR protein is controlled by a suitable expression control sequence operably linked to the nucleic acid sequence. Techniques for operably linking sequences together are well known in the art.

An "expression control sequence" is any nucleic acid sequence that promotes, enhances, or controls expression (typically and preferably transcription) of another nucleic acid sequence. Suitable expression control sequences include constitutive promoters, inducible promoters, repressible promoters, and enhancers. The nucleic acid sequence; encoding the GlyR protein in the vector can be regulated by its endogenous promoter or, preferably, by a non-native promoter sequence. Examples of suitable non-native promoters include the human cytomegalovirus (HCMV) promoters, such as the HCMV immediate-early promoter (HCMV IEp), promoters derived from human immunodeficiency virus (HIV), such as the HIV long terminal repeat promoter, the phosphoglycerate kinase (PGK) promoter, Rous sarcoma virus (RSV) promoters, such as the RSV long terminal repeat, mouse mammary tumor virus (MMTV) promoters, the Lap2 promoter, or the herpes thymidine kinase promoter, promoters derived from SV40 or Epstein Barr virus, and the like. In a preferred embodiment, the promoter is HCMV IEp. In another embodiment, the expression of the nucleic acid sequence encoding the GlyR protein can be controlled by a cell-specific promoter (also referred to as a "tissue-specific" promoter). A promoter is "cell-specific" if its activity is restricted to certain cell types (e.g., neurons). The cell-specific promoter can be any such promoter known in the art. For example, the cell-specific promoter is a promoter that functions only in Aẟ-fibers, peptidergic small unmyelinated C-fibers that project to lamina I and lamina IIo, and non-peptidergic small to medium unmyelinated C-fibers that project to lamina IIiC. In addition, a moveable component of the natural viral latency promoter (LAP2) is active in providing long-term gene expression in both peripheral and brain neurons in animals and can be coupled with nerve specific promoter/enhancers. Alternatively, expression of the nucleic acid sequence encoding the GlyR protein can be controlled by a chimeric promoter sequence. A promoter sequence is "chimeric" if it comprises at least two nucleic acid sequence portions obtained from, derived from, or based upon at least two different sources (e.g., two different regions of an organism's genome, two different organisms, or an organism combined with a synthetic sequence). Alternatively, the promoter can be an inducible promoter, i.e., a promoter that is up- and/or down-regulated in response to an appropriate signal. For example, an expression control sequence up-regulated by a pharmaceutical agent is particularly useful in pain management applications. For example, the promoter can be a pharmaceutically-inducible promoter (e.g., responsive to tetracycline). Examples of such promoters are marketed by Ariad Pharmaceuticals, Inc. (Cambridge, Mass.).

The nucleic acid sequence encoding the GlyR protein can further comprise a transcription-terminating region such as a polyadenylation sequence located 3' of the region encoding the protein. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus).

After the vector has been created, the vector is purified. Vector purification to enhance the concentration of the vector in the composition can be accomplished by any suitable method, such as by density gradient purification, by chromatography techniques, or limiting dilution purification. The vector, preferably a replication-deficient HSV vector, is desirably purified from cells infected with the replication-deficient HSV vector using a method that comprises lysing cells infected with the HSV vector and collecting a fraction containing the HSV vector. The cells can be lysed using any suitable method, such as exposure to detergents, freeze-thawing, and cell membrane rupture (e.g., via French press or microfluidization). The cell lysate then optionally can be clarified to remove large pieces' of cell debris using any suitable method, such as gentle centrifugation, filtration, or tangential flow filtration (TFF). The clarified cell lysate then optionally can be treated with an enzyme capable of digesting DNA and RNA (a "DNase/RNase") to remove any DNA or RNA in the clarified cell lysate not contained within the vector particles.

Generally, the inventive recombinant HSV is most useful when enough of the virus can be delivered to a cell population to ensure that the cells are confronted with a predefined number of viruses. Thus, the present invention provides a stock, preferably a homogeneous stock, comprising the inventive HSV vector. The preparation and analysis of HSV stocks is well known in the art. For example, a viral stock can be manufactured in roller bottles containing cells transduced with the HSV vector. The viral stock can then be purified (for example, on a continuous nycodenze gradient), and aliquotted and stored until needed. Viral stocks vary considerably in titer, depending largely on viral genotype and the protocol and cell lines used to prepare them. Preferably, such a stock has a viral titer of at least about $10^5$ plaque-forming units (pfu), such as at least about $10^6$ pfu or even more preferably at least about $10^7$ pfu. In still more preferred embodiments, the titer can be at least about $10^8$ pfu, or at least about $10^9$ pfu, and high titer stocks of at least about $10^{10}$ pfu or at least about $10^{11}$ pfu are most preferred.

The invention additionally provides a composition comprising the HSV vector and a carrier. The carrier of the composition can be any suitable carrier for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for local (regional) injection or parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to upregulate the body's natural defenses against disease. Antibiotics, i.e., microbicides and fungicides, can be present to reduce the risk of infection associated with gene transfer procedures and other disorders.

The following examples further illustrate the invention but, of course, should not be construed as in any way limiting its scope.

Example 1

This example demonstrates targeted delivery of glycine receptors to peripheral neurons as treatment for pain.

Production of Recombinant Virus.

Figure 1:
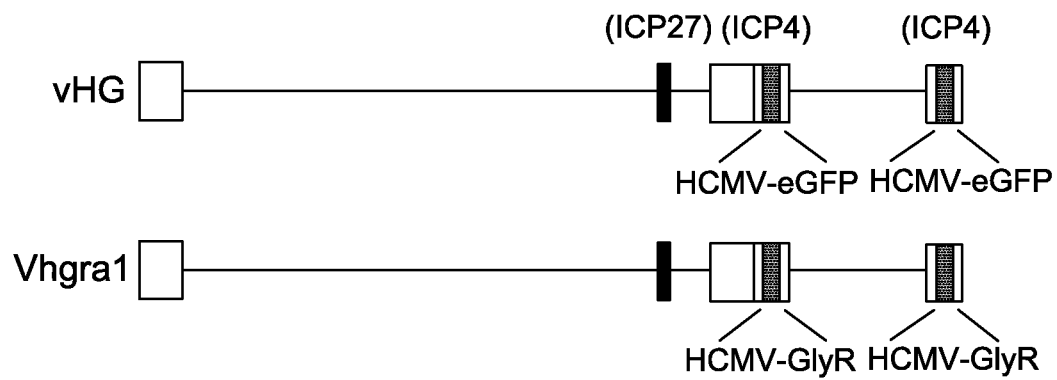
FIG. 1 is a diagram of HSV vector constructs.

The plasmid pSHB2-GlyR was created by cloning the GlyR sequences into plasmid SHB2 at the BamHI site of the polylinker. SHB2 was generated by ligation of a HCMV-BGHpA expression construct from pRC-CMV into plasmid pSASB3 at the unique BamHI site. pSASB3 was constructed by cloning the Sph I to Afl III (Sal I linkered) fragment (1928 bp) of the HSV-1 KOS strain genome (nucleotides 124485-126413) into Sph I/Sal I digested pSP72 followed by insertion of a the 695 bp BglII to BamHI fragment (nucleotides 131931 to 132626) containing regions upstream of the ICP4 promoter including the viral origin contained within the short inverted repeat regions into the BglII to BamHI sites of the vector plasmid. The parental virus vHG was created using the same targeting plasmid except that a HCMV-eGFP construct was cloned into the same BamHI site resulting in the plasmid pSAE3. This plasmid was recombined into an ICP4 and ICP27 deletion KOS strain HSV-1 mutant to produce parental vHG. For vHGlyRα1, candidate plaques were initially selected for the loss of green fluorescence under fluorescent microscopy. GlyR-HSV plaques were purified by three rounds of limiting dilution with the GlyR construct verified by Southern blot analysis. These vectors are schematically represented in FIG. 1.

Functional Assay of Channels In Vitro.

Human embryonic kidney (HEK) 293T cells were maintained as previously described (Qian et al., *J. Physiol.*, 562, 319-31 (2005)). For recordings, HEK 293T cells were plated onto glass coverslips pretreated with poly-D-lysine (0.1 mg/ml) and rat-tail collagen (0.1 mg/ml; BD Biosciences, San Jose, Calif.) in 35 mm culture dishes at $1\text{-}2 \times 10^5$ cells per dish. 24 hours after plating, the cells were infected with the GlyR-HSV construct. For infections the growth medium was removed, the cells were washed twice with serum free growth medium, and vHGlyRα1 was added at a multiplicity of infection (MOI) of 10. The cells were then incubated at 37° C. for 1 hour. Following incubation, 1.5 ml of growth medium (with serum) was added and the cells were incubated for an additional 24 hours at 37° C. Recordings were then performed 24 hours post-infection at room temperature. Glycine-mediated whole-cell currents were recorded with an Axopatch 200 amplifier (Molecular Devices, Union City, Calif.) in voltage-clamp mode. Solutions were delivered via an in-house fabricated fast perfusion system (Qian et al., *J. Physiol.*, 538, 65-77 (2002)). The external solution contains (in mM): 140 NaCl, 5 KCl, 2 $CaCl_2$), 1 $MgCl_2$, and 10 HEPES; pH is 7.2+0.05, adjusted with NaOH and osmolality 290+10 adjusted with sucrose as needed. The internal solution contains (in mM): 140 CsCl, 1 CaCl$_2$), 1 MgCl$_2$, 2 MgATP, 10 HEPES, and 10 EGTA; pH is 7.3+0.05, adjusted with CsOH and osmolality 300+0.05. Data were recorded with a Digidata 1322A digitizer under the control of pClamp 9.2 software (Molecular Devices) and all analyses were performed with Clampfit 9.2 (Molecular Devices) or Origin 7.0 (OriginLab, Northampton, Mass.). Percent desensitization was measured as $100\times(1-I_{SS}/I_{peak})$, where $I_{SS}$ and $I_{Peak}$ are the amplitudes of current at steady state and peak, respectively.

Figure 2:
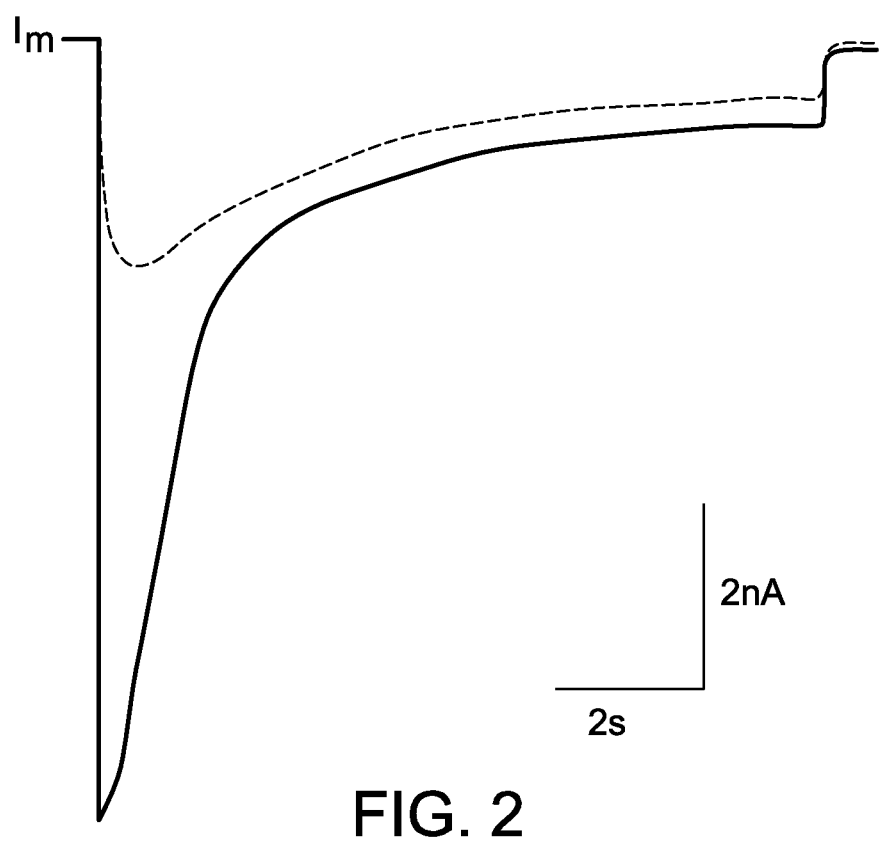
FIG. 2 is a graph demonstrating glycine-induced whole-cell currents ($I_m$) from vHGlyRα1 infected HEK 293T cells.

At 24-hours post-infection, all GlyR-HSV infected cells tested (N=3) displayed glycine-induced whole-cell currents (FIG. 2). In contrast, application of glycine to uninfected HEK 293T cells (N=4) failed to elicit a current response. As expected under the recording conditions used, the glycine-induced currents observed in GlyR-HSV infected cells were large, inward and rapidly desensitizing. As depicted in FIG. 2, mean peak current values were −3.57+0.59 nA (50 uM glycine) and −9.25+1.47 nA (1 mM glycine). Currents became faster (10-90% rise time of 265.2+79.1 vs 11.4+1.0 ms) and percent desensitization increased (73.4+7.3% vs 89.8+1.1%) with increasing glycine concentration.

Cell Culture and Histochemistry.

In order to confirm expression in neurons, dissociated primary doral root ganglia (DRG) neurons were transduced with vHGlyRα1 and examined for glycine receptor expression using immunofluorescent histochemistry. In this respect, dorsal root ganglia (DRGs), which normally do not express GlyRs, from 17-day rat embryos were dissociated with 0.25% trypsin, 1 mM EDTA for 30 minutes at 37° C. with constant shaking and then plated on poly-D-lysine-coated coverslips at $10^5$ cells per well in 24-well plates in 500 µl of defined Neurobasal medium containing B27, Glutamax I, Albumax II, and penicillin/streptomycin (Invitrogen, Carlsbad, Calif.), supplemented with 100 ng/ml of 7.0S NGF per ml (Sigma, St. Louis, Mo.). Fifteen days following plating, cells were transduced with either vHGlyRα1 or vHG at an MOI of 5 for one hour, washed with fresh media, and incubated for an additional 24 hours. Cells were fixed in 4% buffered formalin for 10 minutes, washed 3 times in PBS, and then blocked in 5% normal goat serum, 0.2% tween-20, in PBS for 1 hour at room temperature. Cells were incubated with a monoclonal antibody that specifically recognizes the glycine receptor α-subunit (1:500; Cat #146111, Synaptic Systems, Goettengen, Germany) overnight at 4° C. Some cells were incubated without the primary antibody (primary delete). Cells were washed 3 times in PBS then incubated with AlexaFluor 594 (1:1000, Invitrogen) for 1 hour at room temperature. Cells were washed 3 times in PBS, once in DI water, and mounted onto glass slides with Aqua Poly/Mount (Poly sciences, Warrington, Pa.). Images were acquired on a Zeiss Axiovert 200 microscope using an Axioncam MRCS high resolution camera and Axiovision software (Zeiss, Thronwood, N.Y.).

Twenty-four hours after infection, antibody staining confirmed the presence of α1 GlyR in neurons infected with vHGlyRα1 (FIG. 3, panel A). No α1 GlyR expression was detected in DRG neurons infected with vHG (FIG. 3, panel B) even though robust expression of GFP was observed (FIG. 3, panel D). No immunopositive reaction was observed in cells incubated without the primary antibody (FIG. 3, panel C).

Use of vHGlyRα1 to Treat Pain in a Rat Formalin Model.

For in vivo studies, rats were subcutaneously injected with vHGlyRα1 or vHG, a control vector without α1 GlyR, into the plantar surface of the right hind foot. Analgesic effects of viral injections were assessed one week later by subcutaneous injection of formalin.

Specifically, 3-month-old male Sprague-Dawley rats (225-250 g) were injected with 200 µl ($1\times10^8$ plaque forming units) of either vHGlyRα1 or vHG into the plantar surface of the right hind foot. One week later the analgesic properties of the vectors was assessed by subcutaneously injecting 50 µl of 2.5% formalin into the right hind foot and assessing pain-related behaviors as previously described (Goss et al., *Gene Ther.*, 8, 551-6 (2001)). To examine the effects of activation of expressed GlyR, 50 µl of 100 mM glycine was injected into the plantar surface of the formalin-injected foot. Channels were inhibited by injection of 50 µl of 10 mM strychnine, a specific GlyR inhibitor. The beginning of second phase pain varied between animals from 20 to 40 minutes; this variation was independent of the vector used. Glycine was therefore injected immediately after the 30, 40, or 50 minute observation period and strychnine was injected immediately after the 60, 70, or 80 minute observation period. In order to present the data in a clear manner, this variation was removed from FIG. 4 and all animal data were presented with second phase pain beginning at 20 minutes.

Infection with vHGlyRα1 alone did not have any effect on pain response as injection of formalin resulted in a typical biphasic nociceptive response (FIG. 4A). Second phase pain was significantly reduced in vHGlyRα1-infected animals following injection of glycine at the 30 minute time point (FIG. 4B, black circles), an effect that lasted for the duration of the study. The observed alleviation of pain was reversed by injection of strychnine, a specific GlyR inhibitor, at 60 minutes (FIG. 4B, gray circles). Glycine application resulted in a small, transient, non-significant dip in nociceptive behavior in vHG transfected animals (FIG. 4B, open squares), suggesting that there may be some endogenous glycine-dependent activity; strychnine had no effect in these animals (data not shown). The robust response to added strychnine in reversing the action of added glycine in vHGlyRα1-infected animals strongly indicates that the pain alleviation is primarily due to activation of expressed α1 GlyRs, and cannot be attributed to some indirect effect (e.g., glycine acting as a co-agonist to NMDA receptors).

Use of vHGlyRα1 to Treat Pain in a Rat Osteosarcoma Model.

For the osteolytic sarcoma model, 6 week old C3H/HeJ mice had $10^5$ NCTC 2472 osteolytic sarcoma cells implanted into the medullary space of their right femur as previously described (Goss et al., *Ann. Neurol.*, 52(5): 662-5 (2002)). One week later, some groups of mice were injected with 20 µl ($2\times10^7$ pfu) of either vHGlyRα1 or vHG into the plantar surface of the right hind foot; non tumor implanted mice and tumor implanted mice that received no vector were used as controls. Two weeks after vector injection mice were placed individually into a plastic box and scored for pain-related behavior during open field motor activity by an observer blinded to treatment group using a spontaneous ambulatory pain score graded as: normal (0), slight limp while walking (1); exaggerated limp (missing steps with the affected limb) (2); holding the affected limb elevated while moving or stationary (3); biting and licking the affected limb (4). Mechanical allodynia (MA) was then assessed using an electronic von Frey anesthesiometer (IITC Life Sciences, Inc; Woodland Hills, Calif.) fitted with a semiflexable tip. The next day, all mice were injected with 20 µl of 100 mM glycine into the right footpad, and 15 minutes later spontaneous ambulatory pain and MA were re-assessed. All of the animals treated with the glycine receptor vector demonstrated decreased pain as assessed with both measurements.

This example demonstrates that the inventive method can be used to treat pain in vivo.

Example 2

This example demonstrates a method for inhibiting pain in vivo comprising exogenously expressing a GlyR protein.

The analgesic efficacy of vHGlyRα1 will be assessed in three mouse pain models: (1) the formalin footpad model of acute inflammatory pain, (2) the complete Freund's adjuvant (CFA) model of chronic inflammatory pain, (3) spinal nerve ligation model, (4) the chronic constriction injury (CCI) model of chronic neuropathic pain, and (5) osteolytic sarcoma model of bone cancer pain. Each of these pain models is described in detail below.

Formalin Footpad Test (FFT):

This is an acute model of inflammatory pain (Dubisson and Dennis, Pain, 4(2): 161-74 (1977)). 50 μl of 2.5% formalin will be injected subcutaneously into the plantar surface of the right hind foot. This will cause acute pain lasting approximately 1-2 hours. Following formalin injection, each animal will be placed in a clear rectangular plexiglass cage (20 cm wide×60 cm long×20 cm high). Different positions of the hind paw will be rated continuously over a 3-minute period immediately after injection of the formalin and every 10 minutes thereafter until the pain subsides completely. The following scale will be used: 1=paw rests normally on floor; 2=paw rests lightly on floor, toes ventroflexed; 3=whole paw is elevated; 4=animal licks/bites paw. Weighted pain scores will be calculated by multiplying the amount of time the rat spends in each position according to the following formula: $0*t1+1*t2+2*t3+3*t4/180$; where t1, t2, t3, and t4 are the duration (in seconds) spent in categories 1, 2, 3, and 4 respectively. Rats will be euthanized at the end of the testing and tissue removed for analysis. Sham animals will be injected with PBS.

Complete Freund's Adjuvant Test (CFA):

This is a model of inflammatory pain that better mimics the time course of postoperative pain or other types of persistent injury (Iadarola et al, Brain, 121(Pt 5): 931-47 (1998)). Sprague-Dawley rats will be used in this model. Baseline measurements of mechanical allodynia (MA) and thermal hyperalgesia (TH) will be performed on all rats. 50 μl complete Freund's adjuvant (CFA, undiluted) is injected subcutaneously into the plantar surface of the right hind foot. Injection of CFA will cause an inflammatory response resulting in both mechanical allodynia and thermal hyperalgesia. This reaction usually occurs within 2 hours of injection of CFA and peaks at 8-10 hrs; MA and TH can be assessed several times during this initial phase. Hyperalgesia and edema usually last 1-2 weeks, during which, MA and TH can be assessed.

Spinal Nerve Ligation:

L5 spinal nerve ligation will be used to model neuropathic pain in rats. All surgical instruments will be steam heat sterilized prior to surgery. The instruments will be heat sterilized using a hot bead benchtop sterilizer between animals in a given day. Rats will be anesthetized with ketamine/xylazine (80/10 mg/kg) prior to surgery. The dorsal surface will be palpated to locate the rostral borders of the sacrum and dorsal spinous processes of the lower thoracic and lumbar vertebrae, the T11-T12 laminae will be located by finding the last rib, which attaches to the rostral end of the T13 vertebrae. The hair overlying this area will be cleaned with 70% ethyl alcohol and the surgical field will be shaved and prepared with three alternating scrubs of Betadine and 70% alcohol, and a longitudinal incision will be made exposing several segments of vertebrate. The left paraspinal muscles will be separated from the spinous processes at the L4-S2 levels. The L6 transverse process will be removed with a small rongeur to identify visually the L4-L6 spinal nerves. The left L5 spinal nerve will be isolated and tightly ligated with 3-0 silk thread. The same procedure will be performed on sham-operated animals except for the ligation. Muscle and fascia will be sutured closed and the skin is closed with autoclips, which will be removed after two weeks. The animals will be allowed to recover on a 35° C. heating pad. Post operative plans include penicillin as a prophylactic antibiotic.

Chronic Constriction Injury:

Ligation of the sciatic nerve will be used to model neuropathic pain in mice. All surgical instruments will be steam heat sterilized prior to surgery. The instruments will be heat sterilized using a hot bead benchtop sterilizer between animals in a given day. The hair overlying the right thigh just lateral to the spinal cord will be cleaned with 70% ethyl alcohol, and the surgical field will be shaved and prepared with three alternating scrubs of Betadine and 70% alcohol. A 1-2 cm incision will be made in the skin and the sciatic nerve will be exposed at the level of the middle of the thigh by blunt dissection through the biceps femoris. Proximal to the sciatic nerve's trifurcation, about one cm long area of the sciatic nerve will be cleaned of connective tissue and two ligatures (using 4.0 monofilament) will be tied loosely around the nerve with about 3 mm between each ligation. The ligatures will be tied such that the diameter of the nerve will be just barely constricted when viewed by 30× magnification. This degree of constriction will retard, but not arrest, the circulation through the superficial epineural vasculature and may produce a small, brief twitch in the muscle around the exposure. The incision will be closed in layers. Sham operated control animals will undergo the same procedure but without the sciatic nerve ligature.

Osteolytic Sarcoma Model of Bone Cancer Pain:

This is a pain model that has characteristics of both neuropathic and inflammatory pain. Behavioral testing will be performed following administration of HSV vectors, and includes assaying spontaneous ambulatory pain, mechanical allodynia, and thermal hyperalgesia as discussed below.

The ambulatory behavior of mice implanted with osteolytic sarcoma cells can be graded to assess the degree of nociception. Mice will be placed in a clear plastic 30×20 cm container and observed for problems in spontaneous ambulation during a 2 minute period. The following scores will be given to animals: 0 (normal), 1 (slight limp of implanted limb), 2 (exaggerated limp with some guarding of implanted limb), 3 (excessive guarding of implanted limb and failure to use implanted limb while moving), and 4 (licking and biting of implanted limb).

To assay mechanical allodynia, each animal will be placed into a plexiglass enclosure (23×10 cm for rats, 10×10 cm for mice) on a wire mesh elevated 20 cm above the benchtop. The mechanical threshold will be measured by applying a series of von Frey hairs to the midplantar surface of each hind paw. The von Frey hairs are a set of calibrated filaments of increasing diameter and stiffness. As they are pushed against the bottom of the paw, animals will either retract their foot or not depending if the pressure from the von Frey hair is painful. Withdrawal of the hind paw within 5 seconds will be deemed a positive response; no paw withdrawal will be deemed a negative response. The up-down method will be utilized to determine the 50% gram threshold (Chaplan et al., *J. Neurosci. Methods*, 53(1): 55-63 (1994), and Chaplan et al., *J. Pharmacol. Exp. Ther.*, 269(3): 1117-1123 (1994)). In this respect, a positive response is followed by application of the next grade higher filament and a negative response is followed by presentation of the next grade lower filament; this continues until the 50% gram threshold response is determined.

Thermal hyperalgesia (TH) will be determined using a plantar analgesia meter (IITC Life Sciences, Woodland Hills, Calif.). Each animal will be placed into a plexiglass enclosure and placed on a glass surface maintained at 30° C. After a 15 minute accommodation period, a light beam will be focused onto the midplantar area of each hind paw and the amount of time it takes the animal to move its paw from the heat source will be measured. The heat source automatically turns off if the animal does not respond in 20 seconds in order to ensure that no tissue damage will occur. Three trials will be performed for each side with a 15 minute period between each trial and the times will be averaged.

HSV Vector Footpad Inoculation:

Animals will be anesthetized with Isoflurane. Paper towels will be placed in the bottom of a desiccator jar and a small volume of Isoflurane (0.3 ml per 0.5 L of desiccator space) will be poured onto the towels. A ceramic floor with holes will be placed over the towels and the animals will be placed into the jar with the lid on top until they stop moving. Animals will be removed; a tail and foot pinch will be performed to make sure the animals are fully anesthetized. 100 µl (rats) or 20 µl (mice) of HSV vector (vHGlyRα1 or vHG) will be injected subcutaneously into the midplantar region of the foot using a sterile 0.5 cc insulin syringe with a 30 g attached needle. Animals will be placed back into their cage and allowed to recover (about 5 minutes). This procedure will be performed under a chemical fume hood.

Identification of vHGlyRα1-Infected Cells:

Infected neurons will be identified using a Red gene labeled vector, and Cy5-labeled strychnine will be used to determine the distribution of the GlyR. The response to anesthetics that are known agonists of the GlyR will be assayed to demonstrate their relative activity and effects on nerve conduction. Further nerve conduction studies will be carried out using rat nerve fiber explants infected with the GlyR vector to confirm the activity of GlyR in single neurons. In dose finding and repeat dosing experiments, the method for maximum vector uptake will be determined. The presence of vector will be determined by fluorescence analysis of tissue sections including the sensory ganglia. The vector genome copy number will be determined by quantitative DNA PCR analysis of infected tissue, and the expression of GlyR gene expression will be evaluated by quantitative RT-PCR. The kinetics of GlyR gene expression will be determined when under the control of a more transient promoter (e.g., HCMV) and the long-term promoter (LAP2), a component of the viral latency gene promoter. The co-localization of Red gene expression and immuocytochemistry studies will be used to determine the type of neuron(s) harboring the HSV vector.

Example 3

This example demonstrates a method of generating a transgenic animal that exogenously expresses a GlyR protein.

A cb-stop-lacZ construct (Zinyk et al., *Curr Biol.*, 8(11): 665-8 (1998)) will serve as the base construct for production of transgenic mice. This construct contains (5' to 3') the constitutively active chicken β-actin promoter and the first two non-coding exons, a transcription/translation stop cassette that is flanked by loxP sequences, a lacZ reporter cassette, and the 3' untranslated region/polyadenylation site from the mouse protamine-1 gene. In previous studies of transgenic mice that harbor this construct (see, e.g., Zinyk et al., supra), it was demonstrated that in the absence of Cre-mediated recombination, the reporter cassette was inactive. Following Cre-mediated recombination and deletion of the stop cassette, the reporter cassette was expressed.

Standard molecular techniques will be used to replace the lacZ reporter with either a wild-type or a mutant (M287L) mouse glycine α1 receptor coding sequence. The M287L mutation results in greatly enhanced sensitivity to the volatile anesthetic enflurane. The transgene inserts will be isolated from the plasmid backbone following digestion with Sal1-Asp718, and transgenic mice will be made using standard transgenic pronuclear microinjection techniques at the University of Pittsburgh Transgenic and Gene Targeting Core Facility. C57BL/6J zygotes will be used for pronuclear microinjections. Transgenic founders will be identified by Southern blot or PCR analysis of tail DNA and subsequently bred to C57BL/6J mice to establish the transgenic lines.

To create mice that selectively express a glycine receptor transgene in sensory neurons, transgenic mice will be mated to "knock-in" mice in which Cre recombinase was inserted into the Nav1.8 locus (Stirling et al., *Pain*, 113(1-2): 27-36 (2005)). These mice effectively and selectively induce recombination only in sensory neurons (Stirling et al., supra). Mice that harbor both the glycine receptor and the Nav1.8-Cre transgenes will be compared to nontransgenic controls as well as to each single transgenic line.

Transgene expression and functionality will be analyzed by assaying (1) the distribution of HSV-GlyR in afferent populations, (2) the localization of HSV-GlyR within sensory neurons, (3) the activity of HSV-delivered GlyR protein in transduced afferent populations, (4) the duration of functional GlyR expression, and (5) the functional effects of GlyR activation as a function of the pain model tested. Double and triple label immunohistochemistry will be used to characterize the population of afferents infected with HSV as well as the infection efficiency. Populations to be studied can be broken down into the following categories: (a) myelinated versus unmyelinated using NF200 and peripherin, (b) trophic factor receptor maintaining phenotype: TrkA (small peptidergic), TrkC, GFR-alpha1, GFR-alpha2 and GFR-alpha3, (c) peptide content: CGRP and D34, and (d) nociceptive signaling molecules: TRPV1, TRPA1, NaV1.8, P2X3. The efficiency of labeling will be assessed with the use of retrograde tracers co-injected with HSV. With this approach, the percentage of each type of afferent innervating the site of injection can be determined.

The distribution of functional GlyR within a sensory neuron relative to sites of sensory transduction, action potential generation, action potential propagation, and transmitter release will be assayed using a combination of traditional immunihistochemistry and receptor binding.

To determine the activity of HSV-delivered GlyR protein in transduced afferent populations, a series of electrophysiological studies will be performed on isolated sensory neurons and the isolated sciatic nerve. The isolated sensory neurons will enable characterization of afferent subpopulations in which cutaneous HSV infection results in the generation of functional receptors. The isolated axon preparation will enable determination of whether or not receptors present in mid axons are functional through their ability to block propagated action potentials. A skin-nerve preparation also will be used to determine whether functional receptors are present in afferent terminals.

The duration of functional GlyR expression will be determined using a series of behavioral pharmacological and anatomical approaches. Behavioral experiments will indicate the duration over which functional receptors are present and whether receptor activation influences the duration of receptor expression. The anatomical experiments will be used to assess the time frame over which GlyR and HSV are detected following inoculation.

Incorporated by reference are all references, including publications, patent applications, and patents, cited herein to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of attenuating the sensation of pain in a subject, comprising causing exogenous expression of a glycine receptor alpha 1 (GlyRα1) protein in a peripheral neuron of a subject by introducing a genetic vector into the peripheral neuron, the vector comprising a nucleic acid encoding the GlyRα1 protein in operable linkage to a promoter, to express the GlyRα1 protein in the peripheral neuron wherein the peripheral neuron is associated with the sensation of pain, and subsequently exposing the peripheral neuron to an agonist of the GlyRα1 protein.

2. The method of claim 1, wherein the promoter is a constitutive promoter, an inducible promoter, or a cell-specific promoter.

3. The method of claim 1, wherein the genetic vector is an AAV based vector.

4. The method of claim 1, wherein the genetic vector is a replication-defective HSV vector.

5. The method of claim 1, wherein the agonist comprises glycine.

6. The method of claim 1, wherein the agonist comprises ivermectin.

7. The method of claim 1, wherein the subject is human.

8. The method of claim 1, wherein the GlyRα1 protein comprises a mutein of the GlyRα1 subunit.

9. The method of claim 8, wherein the mutein has altered sites for zinc potentiation or zinc inhibition, anesthetic potentiation, or affinity for an agonist of the mutein.

10. The method of claim 8, wherein the mutein exhibits altered sensitivity and/or selectivity for an agonist of the mutein.

11. The method of claim 8, wherein the mutein exhibits altered affinity for an agonist of the mutein.

12. The method of claim 11, wherein the agonist comprises ivermectin.

13. The method of claim 1, wherein the method reduces regional sensation of pain.

\* \* \* \* \*